(12) United States Patent
Gebauer

(10) Patent No.: US 7,094,352 B2
(45) Date of Patent: Aug. 22, 2006

(54) METHOD AND DEVICE FOR PACKING CHROMATOGRAPHY COLUMNS

(75) Inventor: Klaus Gebauer, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 45 days.

(21) Appl. No.: 10/514,856

(22) PCT Filed: May 30, 2003

(86) PCT No.: PCT/EP03/05712

§ 371 (c)(1),
(2), (4) Date: Nov. 12, 2004

(87) PCT Pub. No.: WO03/101581

PCT Pub. Date: Dec. 11, 2003

(65) Prior Publication Data

US 2005/0236312 A1    Oct. 27, 2005

(30) Foreign Application Priority Data

May 31, 2002    (GB) .................................. 0212513.6

(51) Int. Cl.
*B01D 15/08* (2006.01)
(52) U.S. Cl. ...................... 210/656; 210/198.2; 141/12; 141/80
(58) Field of Classification Search ................ 210/635, 210/656, 198.2, 502.1; 141/12, 80
See application file for complete search history.

(56) References Cited

U.S. PATENT DOCUMENTS

| 3,487,938 | A | * | 1/1970 | Patterson ................. 210/198.2 |
| 3,966,609 | A | | 6/1976 | Godbille et al. |
| 4,450,082 | A | | 5/1984 | Tanouchi et al. |
| 4,675,113 | A | * | 6/1987 | Graves et al. ............... 210/635 |
| 4,927,531 | A | * | 5/1990 | Sakamoto et al. ........ 210/198.2 |
| 5,213,683 | A | | 5/1993 | Mann |
| 5,354,460 | A | | 10/1994 | Kearney et al. |
| 5,902,485 | A | * | 5/1999 | Davis et al. ................. 210/656 |
| 6,576,124 | B1 | * | 6/2003 | Pichl et al. ............... 210/198.2 |
| 6,780,326 | B1 | * | 8/2004 | Egorov et al. .............. 210/656 |
| 2004/0195161 | A1 | * | 10/2004 | Geng et al. ............... 210/198.2 |

FOREIGN PATENT DOCUMENTS

| GB | 2344543 | 6/2000 |
| WO | WO 92/04573 | 3/1992 |
| WO | WO 02/092188 | 11/2002 |
| WO | WO 02/093159 | 11/2002 |

* cited by examiner

*Primary Examiner*—Ernest G. Therkorn
(74) *Attorney, Agent, or Firm*—Yonggang Ji; Dwayne L. Bentley

(57) ABSTRACT

A column comprising a first end (2a) provided with a column packing means and a second end (2b) provided with a fluid collection means for collecting fluid from over some or all of the internal cross-section of the column, wherein said first and second ends (2a, 2b) are held apart by a column wall. The second end (2b) is provided with blocking means (52, 72, 82, 92) movable between a blocking position where said blocking means (52, 72, 82, 92) substantially obstructs the collection of fluid from a predetermined portion (CR, CR1, CR2) of the cross-section of the column and an non-blocking position where it does not substantially obstruct the collection of fluid from the predetermined portion (CR, CR1, CR2) of the cross-section of the column. This allows the resistance to flow through the collection means to be modified to control where the bed media is deposited over the cross-section of the column.

11 Claims, 6 Drawing Sheets

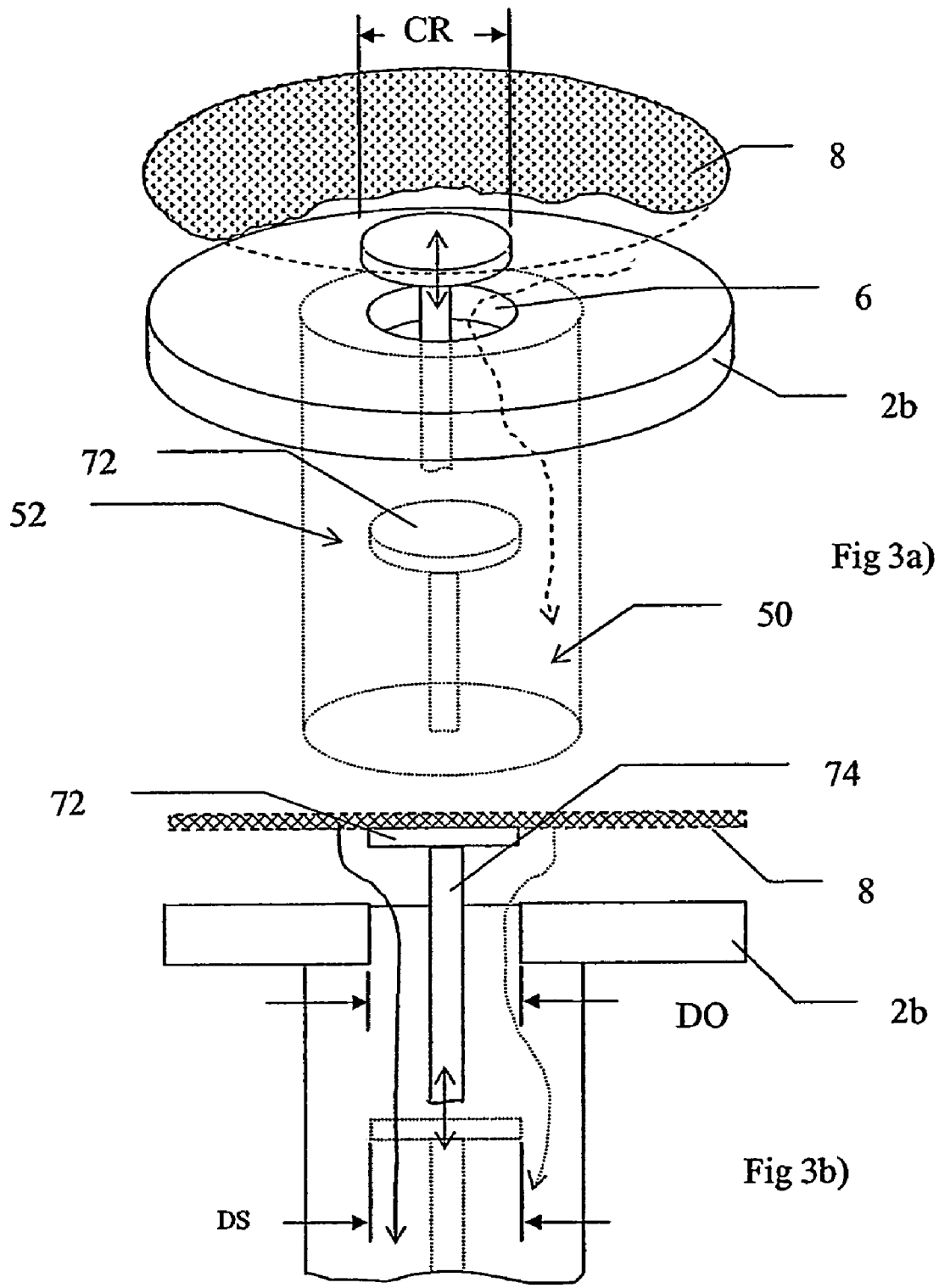

METHOD AND DEVICE FOR PACKING CHROMATOGRAPHY COLUMNS

This application is a filing under 35 U.S.C. 371 and claims priority to international patent application number PCT/EP03/05712 filed May 30, 2003, published on Dec. 11, 2003 as WO 03/101581 and also claims priority to patent application number 0212513.6 filed in Great Britain on May 31, 2002; the disclosures of which are incorporated herein by reference in their entireties.

FIELD OF THE INVENTION

The present invention relates to a packing device and method for use in columns, especially chromatography. More specifically, the invention relates to a packing device and method for improving the packing of chromatography columns, especially columns with a width equal or greater than their height.

BACKGROUND OF THE INVENTION

Columns used in liquid chromatography typically comprise a body-forming structure enclosing a porous media through which a carrier liquid flows, with separation taking place by material collection between the carrier liquid and solid phase of the porous media. Typically, the porous media is enclosed in the column as a packed bed, typically formed by consolidating a suspension of discrete particles. An alternative to the packed bed is the so-called expanded or fluidised bed, where effective porosity and volume of the expanded bed depends on the fluid velocity. The term 'bed' shall be used in the following to describe the porous solid phase in all types of chromatography. The efficiency of the chromatographic separation relies in both modes strongly on the liquid distribution and collection system at the fluid inlet and outlet of the packed bed, and on the homogeneity of the packed bed.

Prior to any separation process, the bed has to be prepared starting from a suspension of particles that has to be introduced into the column. The process of bed formation is called 'packing procedure' and is especially critical for packed beds. The goal of this procedure is to provide a bed of ideal homogeneity. Large scale columns are preferably prepared by injecting a slurry of media particles through a central slurry nozzle. The excess liquid during this procedure is removed at the column outlet, while the particles are retained by means of a filter material, a so-called 'bed support'. The process is complete once the packed bed has completely filled the chromatographic column. The packing process is considered as being successful if the homogeneity and stability of the packed bed allows for a good and robust chromatographic performance quantified in terms of the residence time distribution over the bed. However, if an attempt is made to pack an empty column with bed media using such a slurry nozzle and the bed height is small compared to the column width, then the packing efficiency and bed homogeneity is low. The fluid dynamics of the suspension phase becomes unfavourable such that particles are not distributed and deposited evenly across bed interface. Literally speaking, the jet of suspension leaving the nozzle is not strong enough to transport bed media all the way to the column walls, especially toward the end of the process when the bed interface is in vicinity of the top adapter confining the column at the inlet side. As a result, the bed interface grows with a non-uniform growth rate leading to an uneven bed interface with the maximum height of the interface occurring at a radius smaller than the perimeter of the bed.

Co-pending patent applications GB 0111485.9 and GB0111486.7 describe chromatography devices in which the liquid distribution at the inlet side of the column is achieved by first distributing the liquid radially through one or more horizontal collection slots and then allowing the liquid to enter the column though one or more annular slits arranged intermediate the centre of the column and the wall of the column. A similar liquid collection arrangement is used at the outlet end to collect the liquid leaving the column. Such a liquid collection system is also in operation for removing excess liquid during the packing process and object of the invention.

As used herein and in the appended claims: the term "fluid system" is intended to designate the apparatus in which liquid is either introduced to or withdrawn from a cell at a zone approximately transverse the direction of flow through the cell. The term "cell" is intended to include the terms "vessel" and "column", as well as any other structure utilised by practitioners of the separation arts, to effect a separation, and/or reaction, and/or catalysation and/or extraction of components from an admixture by bringing the admixture into contact with solid or liquid exchange media, above referred to as the packed bed, and/or for the purpose of sintering/consolidating bed material to form a bed, for example a monolithic bed. "Cross-sectional zone" (or region) refers to a region within a cell bounded by cross sections of the cell-oriented transverse (typically approximately normal) the longitudinal direction of flow through the cell. "Longitudinal direction of flow" refers to the direction of flow from an inlet towards an outlet within a cell. "Longitudinal" is used consistently to designate the dominant flow path of fluid through a cell without regard to direction. "Flow connection system" refers to a system of channels or paths that connect two points in a fluid circuit. "Collection system" refers to structures through which fluids are introduced to a cell and "collection system" refers to structures used to withdraw fluids from a cell, in each instance from a cross-sectional zone.

SUMMARY OF THE INVENTION

The object of the invention is to provide a packing device and method for chromatography columns which overcomes the drawbacks of the prior art systems. This is achieved by the device as defined in claim 1 and the method as defined in claim 11.

One advantage with devices and methods in accordance with the present invention is that they provide beds packed to an improved homogeneity.

Embodiments of the invention are defined in the dependent claims.

DETAILED DESCRIPTION OF THE INVENTION

The present invention discloses a packing device and method for packing the bed of chromatography column wherein the column comprising a collection system at the column outlet which collection system is positioned between a bed support and the column outlet and where there is a collection gap between the bed support and the collection system. Devices and methods in accordance with the present invention are applicable to most types of columns and can advantageously be applied to columns in which the collection system comprises collection means e.g. one or more annular slots, or other means, which collect fluid from the collection gap and leads it to the column outlet.

Figure 1:
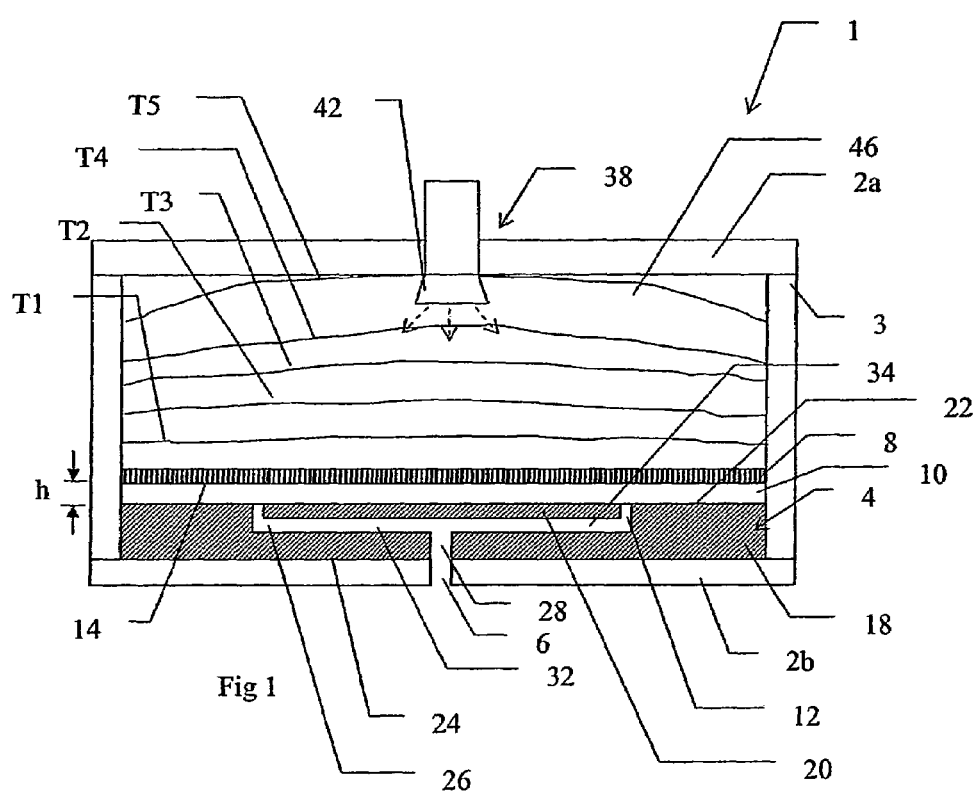
FIG. 1 shows a schematic cross-sectional side view of a chromatography device showing stages in the packing of the media bed without using a packing device or method in accordance with the present invention, FIG. 2a)–2b) are schematic cross-sectional side views of a first embodiment of a chromatography device in accordance with the present invention showing stages in the packing of the media bed, FIG. 3a) is a partial schematic perspective view and FIG. 3b) a cross-sectional side view of a second embodiment of a chromatography device in accordance with the present invention, and, FIG. 4a) is a partial schematic perspective view and FIG. 4b) a cross-sectional side view of a third embodiment of a chromatography device in accordance with the present invention.

FIG. 1 shows schematically a cross-section through a column 1 in which components unrelated to the present invention are omitted for ease of illustration of the principles of the present invention. Column 1 comprises upper and lower end plates 2a, 2b held apart by a cylindrical column wall 3. Both upper and lower end plate may be axially movable in relation to each other such that the distance between the end plates may be adjusted during or after the packing procedure. Lower end plate 2b supports a collection system 4 leading to the column outlet 6, which collection system 4 is positioned between a bed support 8 and the column outlet 6. The bed support may be a perforated plate 8 and if a fine packing material (for example made from discrete particles) is used, the perforated plate 8 may have a fine mesh or an equivalent filter material (not shown) attached on the side facing the bed media to prevent bed media passing through the bed support. There is a collection gap 10 occupying a cross-sectional region of a predetermined height h between the bed support 8 and the collection system 4 and the collection system comprises an annular slot 12. The annular slot is preferably positioned so that less than 50%, most preferably less than 46%, of the internal cross-sectional area of the column is enclosed by it. The collection system 4 is essentially rotationally symmetric and is comprised of a circular main body 18, and a disc shaped collection body 20. The main body 18 has a top surface 22 facing the bed support, a bottom surface 24 facing the lower endplate 2b, and a concentric circular recess 26 formed in the top surface 22. The main body 4 further comprises an outlet connection 28 between the column outlet 6 and the recess 26.

The disc shaped collection body 20 is concentrically arranged in said recess 26 and formed such that an annular collection slot 12 is formed between the inner periphery of the recess 26 and the outer periphery of the disc shaped collection body 20, and that a radial flow connection 32 is formed between the bottom of the disc shaped collection body 20 and the surface 34 of the recess 26 facing it.

The collection system 4 may be comprised of any suitable material, such as a metal, a polymer or the like. Preferably it is made of stainless steel or a rigid polymer that is resistant to all liquid solutions that may be entered into the system. The manufacturing of the components in the collection system 4 may comprise moulding, machining, form pressing and the like. Each of the components in the collection system 4 may be comprised of one solid body or an assembly of two or more sub-bodies, depending on the design of the system.

The top of column 1 is provided with a endplate 2a with a central aperture 38 into which a slurry dispensing arrangement 40 is mountable. The slurry dispensing arrangement comprises a nozzle 42 connected via a pipeline (not shown) to a supply (not shown) of slurry containing bed media particles 46 suspended in a liquid. In order to pack the column with bed media 46, the slurry containing bed media particles 46 is introducable into the column via the pipeline and nozzle 42. The excess liquid during the packing procedure can pass through the bed support and the collection system 4 and is removed from the base of the column though the column outlet 6, while the particles of bed media which are too big to pass through the bed support are retained in the column. FIG. 1 shows profiles of the bed media at five stages T1–T5 during packing of a column. At T1 the bed media is substantially evenly placed over the bed support. At T2 the media bed is slightly thicker in the middle of the column. At T3 the media has started to form a dome and in T4 the dome shape is more pronounced. At T5 the column is filled to the top at the centre of the column while the periphery of the column has voids containing no media. This is caused by the dynamics of the liquid flow in the unpacked column.

Figure 2A:
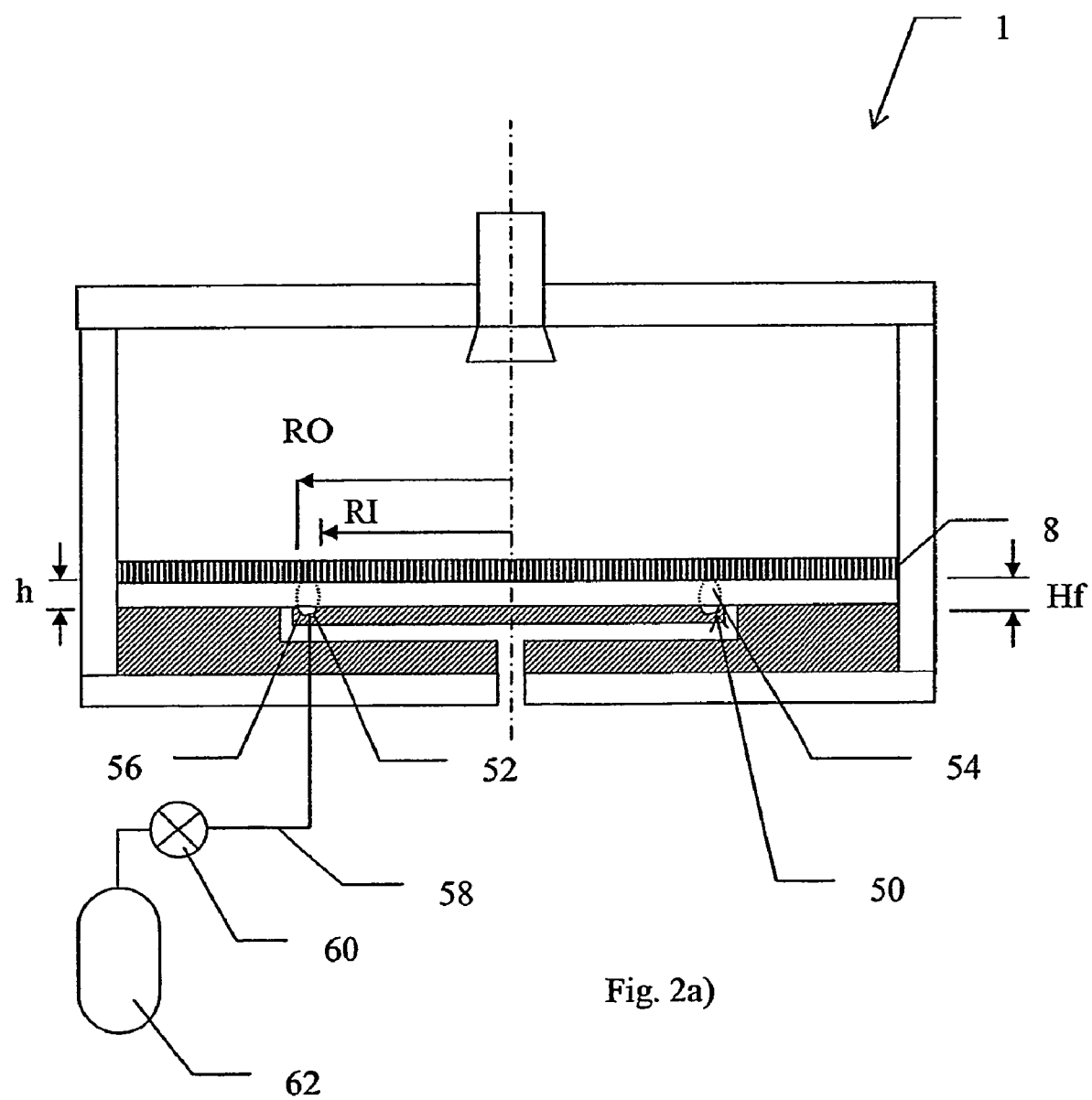
Figure 2B:
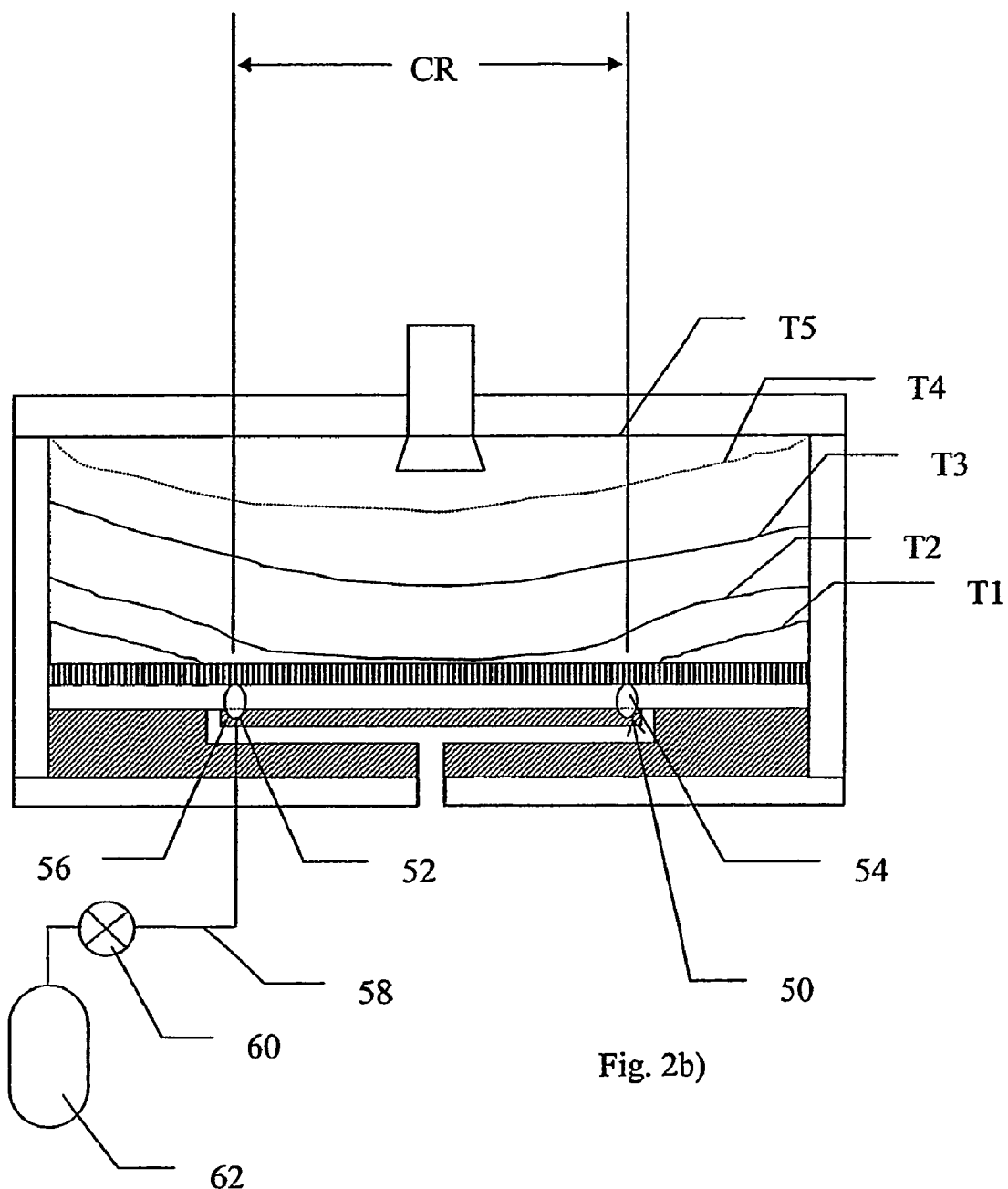

FIG. 2a) shows schematically a cross-section through a column 1 provided with a packing improving device 50 in accordance with a first embodiment of the present invention. This column is similar to the device of FIG. 1 and the same reference numerals will be used for similar parts in all of the figures. The packing improving device 50 comprises a movable shield 52 which is movable between a non-blocking position where it allows liquid to flow unhindered through substantially all of the bed support to the column outlet system, to a blocking position (shown by dotted lines) where it prevents or obstructs the flow of liquid from a predetermined central region of the bed support 8 to the column outlet 6. In this embodiment of the invention the movable shied 52 comprises an inflatable ring 54 of inner radius RI and outer radius RO which is mounted in an appropriately sized circular groove 56 formed concentrically in the surface or on the circumference of disc shaped collection body 20 that is facing the bed support. The free height Hf of inflatable ring 54 when inflated is the same as or greater than the distance h between the disc shaped collection body 20 and the surface of the bed support facing the disc shaped collection body in the region of the disc shaped collection body 20 where the inflatable body is mounted, so that when inflatable body 54 is fully inflated into the blocking position it is in contact with the face of the bed support facing the disc shaped collection body as well as the disc shaped collection body. In this way it blocks the flow of liquid to the column outlet from the region CR enclosed by it. Inflatable ring 54 is connectable via a pipe line 58 and valve 60 to a supply of compressed fluid 62, e.g. air, with a pressure greater than that exerted on the inflatable ring by the contents of the column, or to atmosphere. When packing of the column starts, as shown in FIG. 2b), inflatable ring 54 is inflated with compressed fluid so that it is in the blocking position. This influences the flow of fluid down the column so that the fluid from the packing nozzle is made to flow closer to the column walls than it would do if the inflatable ring 54 was not inflated. This causes the packing media to be deposited nearer to the wall of the column instead of near the centre of the column as shown by time T1. As packing progresses, despite the inflatable ring being inflated, some particles drift towards the centre of column, as shown at T2, so that the deposited bed covers all of the bed support 8, but with a deeper layer of particles nearest the column wall. At time T3, as packing progresses, inflatable ring 54 may be partly deflated (not shown) to allow some fluid flow through the area of the bed support 8 enclosed by it. At T4, when the bed media particles have reach the upper endplate around the periphery of the column, the inflatable ring may be completely deflated (not shown), allowing unobstructed flow thought the area of bed support 8 with a radius of less than RI and at T5 the bed is fully packed, with no voids around the column walls.

FIGS. 3a) and 3b) show schematic perspective, resp. lateral views of the outlet end of a column provided with a second embodiment of the present invention. In this embodiment the column has an outlet endplate 2b with a central outlet 6 and the surface of the end plate facing into the column is provide with fluid collecting system such as radial grooves (not shown) for collecting fluid which passes through bed support 8 The packing improving device 50 comprises a movable shield 52 in the form of a disc 72, with a diameter DS equal to or less than the diameter DO of outlet 6, wherein disc 72 is mounted on a rod 74. Rod 74 is movable by any suitable manual or automated means (not shown) in the longitudinal direction of the column and can move movable shield 52 from a first, non-blocking, position shown by dotted lines where disc 72 is below outlet 6, to a second, blocking, position, shown by solid lines where disc 72 has been moved up through outlet 6 and is in contact with the lower surface of bed support 8. In this blocking position, no fluid can pass through the central portion CR of bed support 8 blocked by disc 72. As packing of the column progresses, disc 72 can be lowered, either in steps or progressively to allow fluid to fluid through the central portion of bed support 8 and packing media to be deposited there.

Figure 4A:
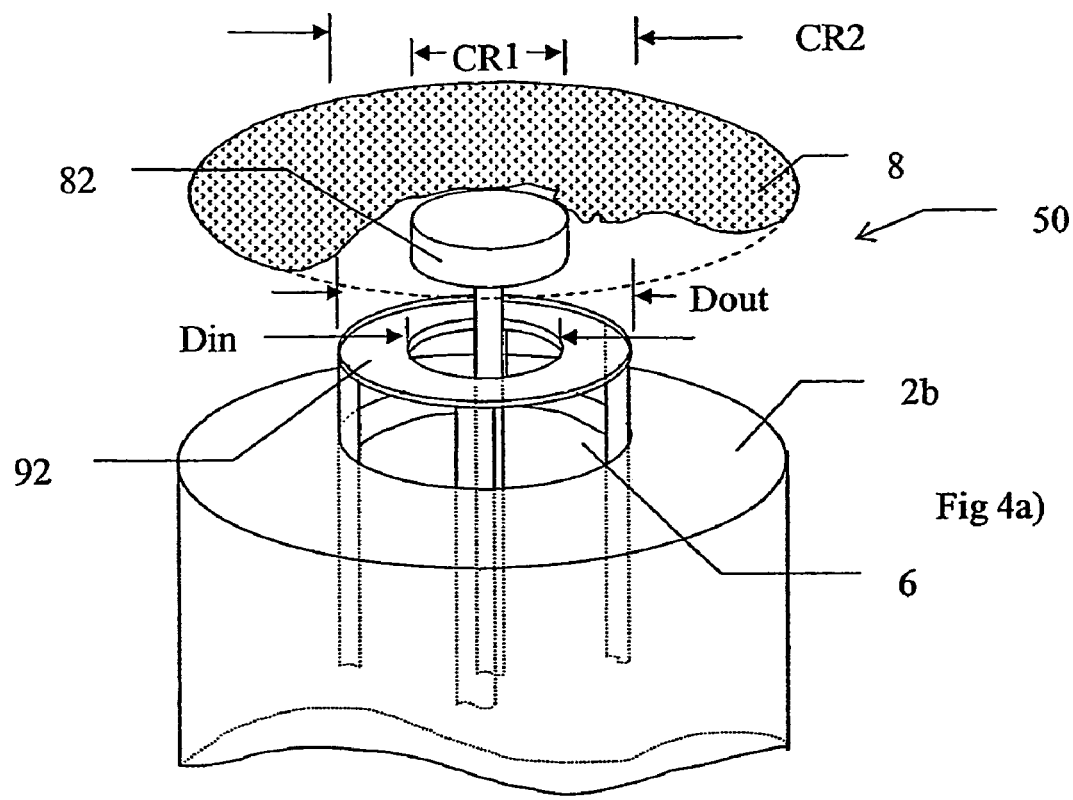

FIGS. 4a) and 4b) show schematic perspective, resp. lateral views of the outlet end of a column provided with a third embodiment of the present invention. In this embodiment the column has an outlet endplate 2b with a central outlet 6 and the surface of the end plate facing into the column is provide with fluid collecting system such as radial grooves (not shown) for collecting fluid which passes through bed support 8. The packing improving device 50 comprises two movable shields. The first movable shield is in the form of a disc 82, with a diameter DS less than the diameter DO of outlet 6, preferably less than 70% of the diameter DO, wherein disc 82 is mounted on a rod 84. Rod 84 is movable by any suitable manual or automated means (not shown) in the longitudinal direction of the column and can move movable shield 52 from a first, non-blocking, position shown by dotted lines where disc 82 is below outlet 6, to a second, blocking, position, shown by solid lines where disc 82 has been moved up through outlet 6 and is in contact with the lower surface of bed support 8. In this blocking position, no fluid can pass through the central portion CR1 of bed support 8 blocked by disc 82. As packing of the column progresses, disc 82 can be lowered, either in steps or progressively to allow fluid to fluid through the central portion of bed support 8 and packing media to be deposited there. In this way the distribution of the bed media deposited on the bed support can be controlled.

Figure 4B:
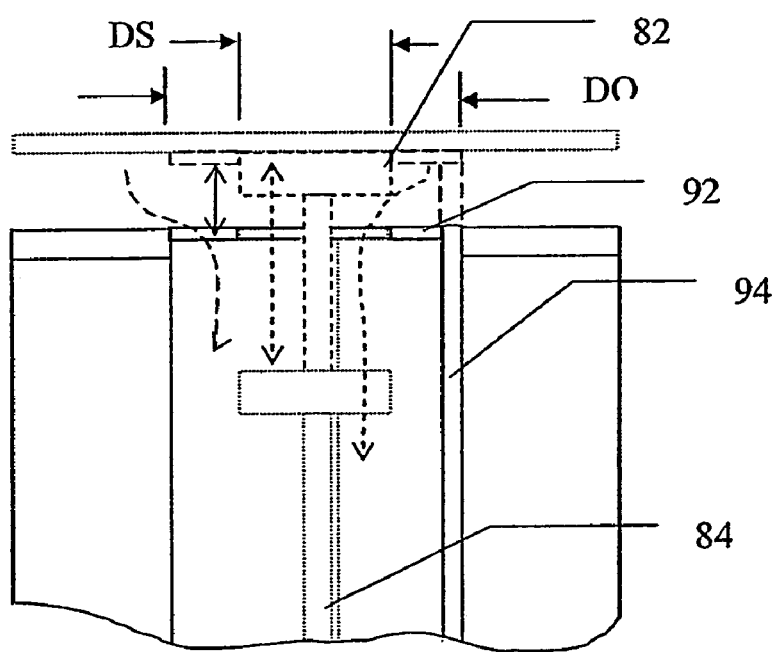

The second movable shield is in the form of a flat ring 92, with an outer diameter Dout which, in this example, is equal to or just less than the diameter DO of outlet 6, and an inner diameter Din which, is just greater or equal to the diameter DS of disc 82. Ring 92 is mounted on a plurality of legs 94 attached to the lower surface of ring 92 and spaced around the periphery of ring 92. Legs 94 are movable by any suitable manual or automated means (not shown) in the longitudinal direction of the column and can move ring from a first, non-blocking, position shown by solid lines in FIG. 4b lines where the top surface of ring 92 is co-planer with the top surface of end plate 2b, to a second, blocking, position, shown by dashed lines where ring 92 has been moved up through outlet 6 and is in contact with the lower surface of bed support 8. In this blocking position, no fluid can pass through the intermediate portion (CR2–CR1) of bed support 8 blocked by ring 92. Ring 92 can be lowered, either in steps or progressively, to allow progressively less restricted flow through the intermediate area.

When the column is to be packed both disk 82 and ring 92 are raised so that they are in contact with the bottom surface of bed support 8. Preferably disc 82 and ring 92 are provided with sealing means (not shown) between the circumference of disc 82 and the inner circumference of ring 92 to prevent leakage. This prevents fluid flowing through the central portion CR2 of bed support 8 which extends from the centre to a distance of Dout/2. As packing progresses ring 92 can be lowered progressively or in steps in order to allow some fluid to pass thought the intermediate area of the bed support that it was in contact with and to allow bed media to build up on the bed support there. Similarly disc 82 can be lowered progressively or in steps in order to allow some fluid to pass thought the area of the bed support that it was in contact with and to allow bed media to build up on the bed support there. In this way the distribution of the bed media deposited on the bed support can be controlled.

Figure 5:
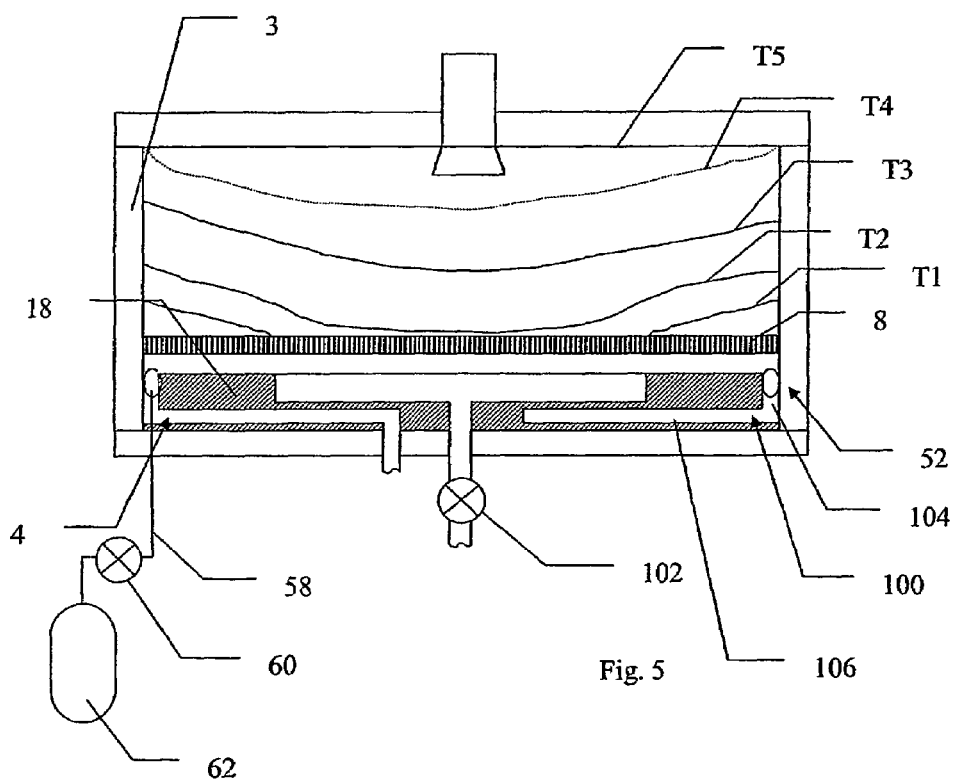
FIG. 5 shows schematically a cross-section through a column provided with a packing improving means in accordance with a further embodiment of the present invention.

FIG. 5 shows a schematically a cross-section through a column 1 provided with a packing improving means in accordance with a further embodiment of the present invention. The packing improving means comprises a secondary flow path 100 which is arranged to collect liquid from the periphery of the column, a movable shield 52 which can prevent the flow of liquid in said secondary flow path 100 and a flow obstructing means such as a valve 102 for preventing or restricting the flow of liquid through the column outlet 6. Secondary flow path can be in the form of an annular peripheral slot 104 provided between the circular main body 18 of the collection system 4 and the column wall 3, the annular peripheral slot 104 being joined by a radial passage 106 in the circular main body 18 to a secondary flow path outlet 108. Movable shield can be in the form of an inflatable ring 54 which is mounted in annular peripheral slot 104. Inflatable ring 54 is connectable via a pipe line 58 and valve 60 to a supply of compressed fluid 62, e.g. air, with a pressure greater than that exerted on the inflatable ring by the contents of the column, or to atmosphere. When packing of the column starts inflatable ring 54 is deflated so that it is not in the blocking position and valve 102 is closed so that no liquid can flow through column outlet 6. This influences the flow of fluid down the column so that the fluid from the packing nozzle is made to flow closer to the column wall 3 than it would do if valve 102 was open. This causes the packing media to be deposited nearer to the wall of the column instead of near the centre of the column as shown by time T1. As packing progresses, despite the valve 102 being closed, some particles drift towards the centre of column, as shown at T2, so that the deposited bed covers all of the bed support 8, but with a deeper layer of particles nearest the column wall. At time T3, as packing progresses, inflatable valve 102 may be moved to an intermediate position where it is partly open in order to allow some fluid flow through the centre of the bed support 8. At T4, when the bed media particles have reach the upper endplate around the periphery of the column, the inflatable ring may be inflated preventing flow though the annular peripheral slot, while at the same time valve 102 may be fully opened to facilitate flow through the centre of the column and leading to more bed media particles being deposited in the centre of the column At T5 the bed is fully packed, with no voids around the column walls. During subsequent use of the column, inflatable ring 54 is kept inflated in order to prevent the liquid in the column from entering secondary flow path 100.

While the invention has been illustrated by means of examples showing one and two movable shields, it is of course possible to use more shields. It is furthermore conceivable to provide a column with a combination of the embodiments of the present invention described above.

In order to prevent microbial growth in the flow channels that are only used during packing, once the column has been packed he channels can be unblocked and the column flushed with ethanol or other microbe killing-substance. The microbe-killing substance can then be flushed out of the column before it is put into use.

The invention is not limited to columns having circular cross-sections but can be adapted to columns of any cross-sectional shape, e.g. square, polygonal, semicircular, etc.

Preferably when only one shield is used then when it is in the maximum blocking position, i.e. the position where it obstructs flow thought the bed support the most, it shields an area which is from 10% to 90% of the cross-sectional area of the column. Preferably it shields an area that is between 20% and 80% of the cross-sectional area.

If more than one shield is used, then when all the shields are in use in the maximum blocking position, they preferably obstruct flow though an area which is between 10% to 90% of the cross-sectional area of the column. Preferably they shield an area that is between 40% and 80% of the cross-sectional area. Preferably the dimensions of the shields are arranged so that when each outer shield is moved from the blocking position to the non-blocking position then the remaining blocked area is about half the size of the area that was blocked when the shield was in the blocking position.

Once a column has been packed, the bed may remain in the column and used in situ. Alternatively the packed bed may be removed from the column as a block and transferred to another column. Thus a sophisticated, dedicated bed-packing column in accordance with the present invention can be used, for example, to pack a bed to form a homogeneous monolithic bed. The homogeneous bed can then be removed and transported in a simple container to a simpler column where it is subsequently used.

The invention is not intended to be limited to the above embodiments but is able to be modified in accordance with the following claims.

What is claimed is:

1. A column comprising a first end (2*a*) provided with means to added media particles, and a second end (2*b*) provided with a fluid collection means for collecting fluid from over some or all of the internal cross-section of the column, wherein said first and second ends (2*a*, 2*b*) are held apart by a column wall, and wherein said second end (2*b*) is provided with blocking means (52, 72, 82, 92, 102) movable between a blocking position where said blocking means (52, 72, 82, 92, 102) substantially obstructs the collection of fluid from a predetermined portion (CR, CR1, CR2) of the cross-section of the column while permitting the collection of fluid from another portion of the cross-section of the column, and a non-blocking position where it does not substantially obstruct the collection of fluid from the predetermined portion (CR, CR1, CR2) of the cross-section of the column.

2. The column of claim 1, wherein the predetermined portion of the cross-section is a central portion (CR, CR1) of said cross-section.

3. The column of claim 1, wherein the predetermined portion extends from the centre of the column and covers an area which is between 0.1 to 0.9 of the internal cross-sectional area of said column.

4. The column of claim 1, wherein the predetermined portion extends from the centre of the column covers an area which is between 0.2 to 0.8 of the internal cross-sectional area of said column.

5. The column of claim 1, wherein the predetermined portion extends from the centre of the column covers an area which is between 0.2 and 0.5 of the internal cross-sectional area of said column.

6. The column of claim 1, wherein the predetermined portion extends from the centre of the column covers an area which is less than or equal to 0.5 of the internal cross-sectional area of said column.

7. The column of claim 1, wherein a plurality of blocking means (52, 72, 82, 92, 102) is provided, each movable between a blocking position where said blocking means substantially obstructs the collection of fluid from a predetermined portion (CR, CR1, CR2) of the cross-section of the column and an open position where it does not substantially obstruct the collection of fluid from the predetermined portion of the cross-section (CR, CR1, CR2) of the column.

8. The column of claim 1, wherein the blocking means comprises an inflatable ring (54).

9. The column of claim 1, wherein the blocking means comprises a movable blanking plate (72, 82, 92).

10. The column of claim 1, wherein the blocking means (52, 72, 82, 92, 102) is movable to an intermediate position between said blocking position and said open position in which it substantially obstructs the collection of fluid from a predetermined portion (CR, CR1, CR2) of the cross-section of the column less compared to when it is in the blocking position and more compared to when it is in the open position.

11. A method for packing a column including a first end (2*a*), bed media inlet means, and a second end (2*b*) provided with a fluid collection means for collecting fluid from over some or all of the internal cross-section of the column, wherein said first and second ends (2*a*, 2*b*) are held apart by a column wall, comprising the steps of:
providing said column with the blocking means (52, 72, 82, 92, 102) of claim 1;
moving said blocking means (52, 72, 82, 92, 102) to said first blocking position;
filling said column partially with bed media;
moving said blocking means (52, 72, 82, 92, 102) to said unblocking position; and
completing the filling of said column with bed media.

* * * * *